US00PP13724P39

(12) United States Plant Patent

Yomo et al.

(10) Patent No.: US PP13,724 P3

(45) Date of Patent: Apr. 15, 2003

(54) VERBENA PLANT NAMED 'SUNVIVARO'

(75) Inventors: Yasunori Yomo, Yasu-gun (JP); Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/987,810

(22) Filed: Nov. 16, 2001

(65) Prior Publication Data

US 2002/0029396 P1 Mar. 7, 2002

Related U.S. Application Data

(63) Continuation of application No. 09/375,362, filed on Aug. 17, 1999.

(51) Int. Cl.[7] ..... A01H 5/00

(52) U.S. Cl. ..... Plt./308

(58) Field of Search ..... Plt./308

(56) References Cited

U.S. PATENT DOCUMENTS

| | | | | |
|---|---|---|---|---|
| PP8,995 P | 11/1994 | Tachibana et al. | ..... | Plt./308 |
| PP9,014 P | 12/1994 | Tachibana et al. | ..... | Plt./308 |
| PP9,059 P | 2/1995 | Tachibana et al. | ..... | Plt./308 |
| PP9,085 P | 3/1995 | Tachibana et al. | ..... | Plt./308 |
| PP9,121 P | 4/1995 | Tachibana et al. | ..... | Plt./308 |
| PP9,411 P | 12/1995 | Tachibana et al. | ..... | Plt./308 |
| PP10,311 P | 3/1998 | Tachibana | ..... | Plt./308 |
| PP10,705 P | 11/1998 | Tachibana | ..... | Plt./308 |
| PP10,743 P | 1/1999 | Nagase | ..... | Plt./308 |
| PP10,755 P | 1/1999 | Nagase | ..... | Plt./308 |
| PP10,801 P | 2/1999 | Nagase | ..... | Plt./308 |
| PP11,037 P | 8/1999 | Yomo et al. | ..... | Plt./308 |

OTHER PUBLICATIONS

GTITM UPOVROM Citation for 'Sunvivaro' as per JP PBR 9055; Sep. 4, 1996.*

* cited by examiner

*Primary Examiner*—Kent Bell

(74) *Attorney, Agent, or Firm*—Burns, Doane, Swecker & Mathis, LLP

(57) ABSTRACT

Disclosed herein is a verbena plant which has erect growth habit and good plant height. The plant forms plentiful flowers in a spike in great profusion. The blooming period is late April to November and the flowering duration is long. The entire plant commonly remains in bloom for a considerable period of time. The flower size is large and the petal color is vivid purplish red without an eye. The plant is highly tolerant to heat, and has high resistances to pests and diseases, particularly powdery mildew, and high resistance to rain.

2 Drawing Sheets

This application is a continuation of application Ser. No. 09/375,362, filed on Aug. 17, 1999.

BOTANICAL/COMMERCIAL CLASSIFICATION

*Verbena peruviana*/Verbena Plant.

VARIETAL DENOMINATION cv. 'Sunvivaro'.

BACKGROUND OF THE VARIETY

The present invention relates to a new and distinct variety of Verbena plant obtained from crossing a wild type of Verbena plant *Verbena peruviana* (♀) native to Brazil and another wild type of Verbena plant *Verbena peruviana* (♂) native to Brazil.

Verbena is a very popular plant and is used for flower bedding and potting in the summer season. There are only a few varieties of Verbena plants having much branching, many flowers in a spike, a long flowering duration and which have a high resistance to rain, heat, cold, and disease. Accordingly, this invention was aimed at obtaining a new variety having an erect growth habit, strong branching, many flowers in a spike, long flowering duration, high tolerance to heat and cold, and resistances to diseases and pests, and also having petals that are vivid purplish red.

The new variety of Verbena plant according to this invention originated from crossing of a wild type of Verbena plant *Verbena peruviana* (♀) native to Brazil and another wild type of Verbena plant *Verbena peruviana* (♂) native to Brazil.

First of all, 32 seedlings were obtained in the autumn of 1993, from crossing a wild type of Verbena plant 'VBA' (*Verbena peruviana* f. rosea—non-patented in the United States) as female parent and another wild type of Verbena plant 'VBB' (*Verbena peruviana* f. rosea—non-patented in the United States) as pollen parent in the spring of 1993. From this crossing, one seedling was selected in view of erect growth habit, branching and petal color, and propagated by cutting, and then grown as a trial in flower beds and planters from the spring of 1994. Finally a trial by flower potting and bedding was carried out on the selected one plant to the autumn of 1995. The botanical characteristics of the selected one seedling were examined, using similar varieties 'Sunvivapa' (Appl. No. 8239 under the Seeds and Seedlings Law of Japan and U.S. Plant patent application No. 09/987,811, filed Nov. 16, 2001) and 'Showtime Blaze' (non-patented in the United States) for comparison. As a result, it was concluded that this Verbena is distinguishable from any other variety whose existence is known to us, and is uniform and stable in its characteristics. This new variety of Verbena plant was named 'Sunvivaro'.

In the following description, the color-coding is in accordance with The Horticultural Colour Chart of The Royal Horticultural Society, London, England (R.H.S. Colour Chart), and the Inter-Society Color Council-National Bureau of Standards Color Name (I.S.C.C.-N.B.S. Color Name). A color chart based on The Japan Color Standard for Horticultural Plant (J.H.S. Color Chart) is also added for reference.

The female parent 'VBA' and the pollen parent 'VBB', used in the obtaining of this new variety 'Sunvivaro', are wild types of Verbena native to South Brazil.

The new variety of the present invention can be readily distinguished from its 'VBA' and 'VBB' parental varieties. More specifically, the new variety forms vivid purplish red flowers and the parental varieties each form blue flowers.

The 'Showtime Blaze', used as a comparison for this new variety 'Sunvivaro', is commercially available. The petal color of 'Showtime Blaze' is similar to that of 'Sunvivaro'. The main botanical characteristics of 'Showtime Blaze' are as follows:

Plant:
- *Growth habit.*—Erect.
- *Plant extension.*—Medium.
- *Plant height.*—High. (25–35 cm).

Stem:
- *Diameter.*—Medium.
- *Anthocyanin pigmentation.*—Absent.
- *Pubescence.*—Present.
- *Prickle.*—Absent.
- *Branching.*—Medium.
- *Subterranean stem.*—Absent.
- *Length of internode.*—Medium. (3–4 cm).

Leaf:
- *Phyllotaxis.*—Opposite.
- *Shape of blade.*—Hastate.
- *Blade incision.*—Present.
- *Depth of blade incision.*—Shallow.
- *Shape of leaf margin.*—Serrated.
- *Length.*—Medium.
- *Width.*—Medium.
- *Color.*—Dark green. (R.H.S. Colour Chart No. 137B, JHS Color Chart No. 3508).
- *Pubescence.*—Present.
- *Petiole.*—Absent.

Flower:
- *Shape of cluster.*—Obconical.
- *Spike length.*—Medium.
- *Spike diameter.*—Medium.
- *Facing direction.*—Upward.
- *Outward curvature of petal.*—Curved.
- *Diameter.*—Large.
- *Height.*—Long.
- *Color of petal.*—Deep reddish orange (R.H.S. Colour Chart No.47A, J.H.S. Color Chart No.0708).
- *Eye color.*—Absent.
- *Variegation.*—Absent.
- *Color presentation.*—Substantially even.
- *Overlapping of petals.*—Separate.
- *Incision of petal.*—Present.
- *Number of petals.*—Medium.
- *Calyx incision.*—Present.
- *Calyx length.*—Long.
- *Anthocyanin pigmentation of calyx limb.*—Present.
- *Pistil shape.*—Two lobes.
- *Stamen number.*—Medium.
- *Anther color.*—Yellowish green.
- *Peduncle diameter.*—Thin.
- *Peduncle length.*—Short.
- *Number of flowers.*—Medium.
- *Flower fragrance.*—Absent.
- *Flowering time.*—Medium.
- *Flowering duration.*—Medium.

Physiological and ecological characteristics:
- *Tolerance to cold.*—Medium.
- *Tolerance to heat.*—Low.
- *Resistance to diseases.*—Low.
- *Resistance to pests.*—Low.

The main botanical characteristics of 'Sunvivapa' are as follows:

Plant:
- *Growth habit.*—Erect.
- *Plant extension.*—Medium.
- *Plant height.*—High. (40–50 cm).

Stem:
- *Diameter.*—Medium. (2–3 mm).
- *Anthocyanin pigmentation.*—Present.
- *Pubescence.*—Dense.
- *Prickle.*—Absent.
- *Branching.*—Abundant.
- *Subterranean stem.*—Absent.
- *Length of internode.*—Medium. (4–5 cm).

Leaf:
- *Phyllotaxis.*—Opposite.
- *Shape of blade.*—Hastate.
- *Blade incision.*—Present.
- *Depth of blade incision.*—Shallow.
- *Shape of leaf margin.*—Crenate.
- *Length.*—Medium. (4–5 cm).
- *Width.*—Medium. (3 cm).
- *Color.*—Moderate Olive green. (R.H.S. Colour Chart No. 146A, J.H.S. Color Chart No. 3509).
- *Pubescence.*—Present.
- *Petiole.*—Present.
- *Petiole diameter.*—Medium.
- *Petiole length.*—Medium.

Flower:
- *Shape of cluster.*—Funnel-shaped.
- *Spike length.*—Medium. (3 cm).
- *Spike diameter.*—Large. (4–5 cm).
- *Facing direction.*—Upward.
- *Outward curvature of petal.*—Slightly curved.
- *Diameter.*—Large. (20–30 mm).
- *Height.*—Long.
- *Color of petal.*—Deep reddish purple. (R.H.S. Colour Chart No. 78A, J.H.S. Color Chart No. 8907).
- *Eye color.*—Absent.
- *Variegation.*—Absent.
- *Color presentation.*—Substantially even.
- *Overlapping of petals.*—Separate.
- *Incision of petal.*—Present.
- *Number of petals.*—Medium.
- *Calyx incision.*—Present.
- *Calyx length.*—Medium.
- *Anthocyanin pigmentation of calyx limb.*—Present.
- *Pistil shape.*—Two lobes.
- *Stamen number.*—Medium.
- *Anther color.*—Yellowish green.
- *Peduncle diameter.*—Medium.
- *Peduncle length.*—Medium.
- *Number of flowers.*—Medium.
- *Flower fragrance.*—Absent.

*Flowering time.*—Late.
*Flowering duration.*—Long.
Physiological and ecological characteristics:
*Tolerance to cold.*—High.
*Tolerance to heat.*—High.
*Resistance to diseases.*—High.
*Resistance to pests.*—High.

The new variety of Verbena plant 'Sunvivaro' was asexually reproduced by cutting at the aforementioned Hakushu Nursery Center of SUNTORY Ltd., residing at 29131 Torihara, Hakushu-cho, Kitakoma-gun, Yamanashi-ken, Japan, and the homogeneity and stability thereof were confirmed. The instant plant retains its distinctive characteristics and reproduces true to type in successive generations.

SUMMARY OF THE VARIETY

This new variety of Verbena plant has erect growth habit and the plant height is high. The plant has many branches and plentiful flowers in a spike, and a great profusion of blooms. The blooming period is late April to November and the flowering duration is long. The whole plant remains in bloom for a considerable period of time. The flower petal color is vivid purplish red color and there is no eye. The plant is highly tolerant to heat, and has a high resistance to pests and diseases, particularly powdery mildew and high resistance to rain. Medium resistance to cold.

DESCRIPTION OF THE VARIETY

Figure 1:
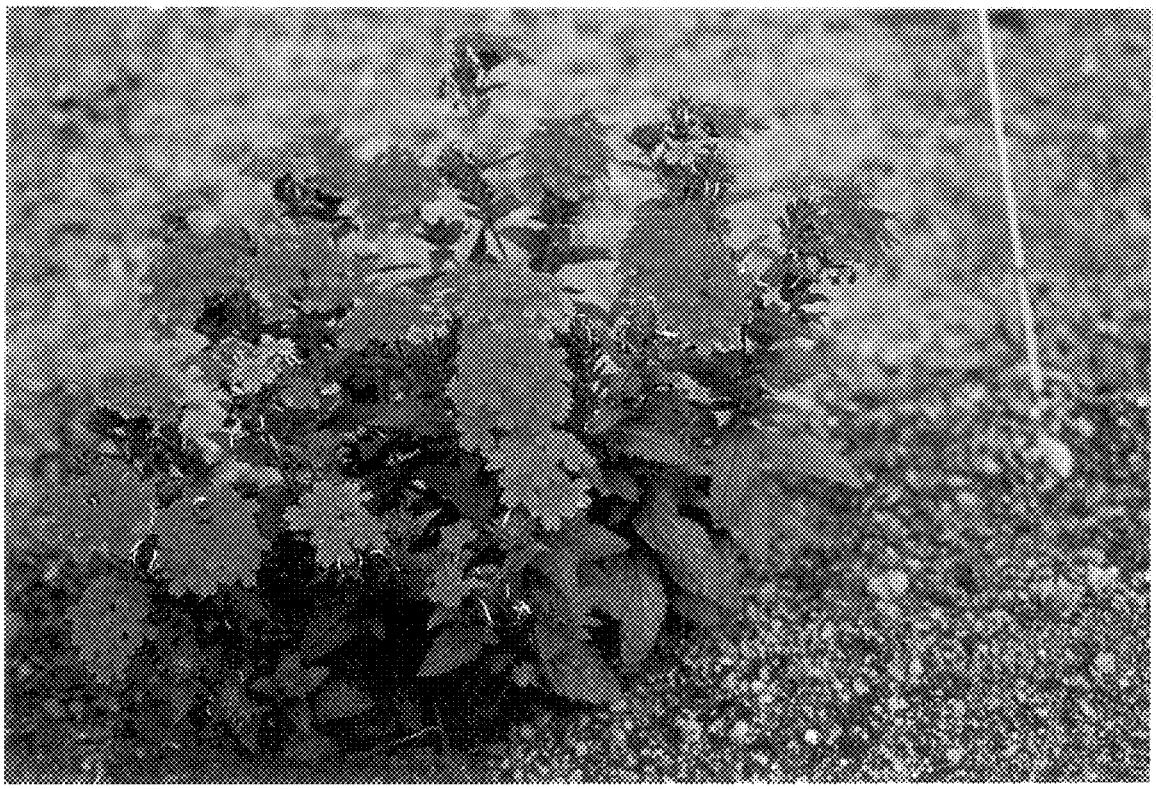
FIG. 1 is a photograph giving a view of the new variety of Verbena plant growing in the ground.
Figure 2:
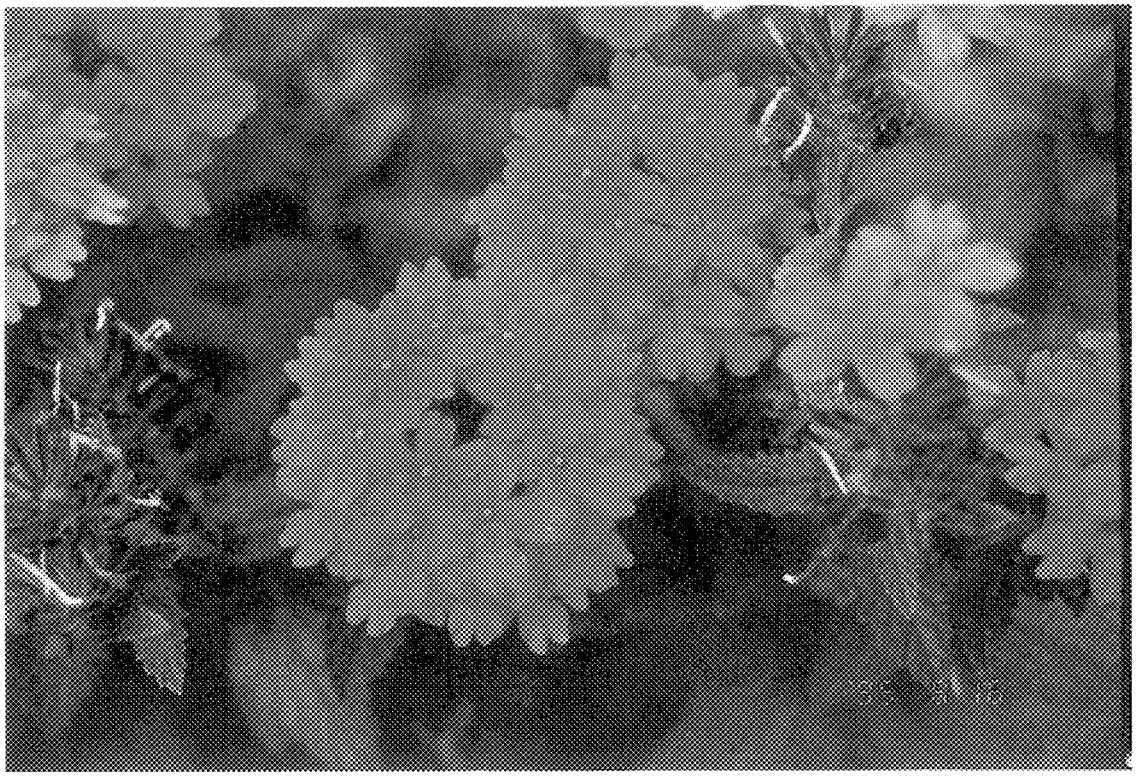
FIG. 2 is a photograph of flowers of the new variety of Verbena plant.

The plants described hereafter were approximately eight months of age following the rooting of cuttings and were observed in August while growing at Mishima-gun, Oosaka-fu, Japan. Finished plants were produced eight months after the rooting of cuttings.

The botanical characteristics of the new and distinct variety of Verbena plant, 'Sunvivaro' are as follows:

Plant:
*Growth habit.*—Erect.
*Plant extension.*—Medium.
*Plant height.*—Medium to high. (25–29 cm).
*Plant width.*—Approximately 27 cm.
Stem:
*Typical stem length.*—Approximately 22 cm.
*Diameter.*—Medium. (1.4–3.0 mm).
*Anthocyanin pigmentation.*—Absent.
*Pubescence.*—Present in a moderate quantity.
*Branching.*—Medium with a typical finished plant commonly displaying approximately ten branches.
*Subterranean stem.*—Absent.
*Length of internode.*—Short. (1.0–1.8 cm).
Leaf:
*Phyllotaxis.*—Opposite.
*Shape of blade.*—Hastate.
*Blade incision.*—Pinatilobed.
*Depth of blade incision.*—Shallow.
*Shape of leaf margin.*—Dentate.
*Length.*—Medium, and commonly approximately 3.8 cm on average.
*Width.*—Medium, and commonly approximately 1.7 cm on average.
*Base.*—Wedge-shaped.
*Apex.*—Acute.
*Venation.*—Pinnate.
*Color.*—Grayish olive green. (R.H.S. Colour Chart No. 137A, J.H.S. Color Chart No. 3716) on the upper surface, and R.H.S. Colour Chart No. 146C on the under surface.
*Pubescence.*—Sparse.
*Petiole.*—Present.
*Petiole diameter.*—Medium, and commonly approximately 1.8 mm.
*Petiole length.*—Short, and commonly approximately 2.6 mm.
*Petiole color.*—R.H.S. Colour Chart No. 144A.
Flower:
*Shape of cluster.*—Funnel-shaped.
*Spike length.*—Medium. (2.0–4.3 mm).
*Spike diameter.*—Medium to large. (4.5–5.4 mm).
*Facing direction.*—Upward.
*Outward curvature of petal.*—Slightly curved.
*Bud length.*—Commonly approximately 1.2 cm.
*Bud diameter.*—Commonly approximately 2 mm.
*Bud color.*—R.H.S. Colour Chart No. 144A.
*Bud shape.*—Cup-shaped upon opening.
*Diameter.*—Large. (18–22 mm).
*Floral tube.*—Commonly approximately 1.5 cm in length.
*Petal base.*—Tubular.
*Petal apex.*—Notched.
*Petal margins.*—Smooth.
*Petal texture.*—Matt.
*Color of petal.*—Vivid purplish red (R.H.S. Colour Chart No. 66A, J.H.S. Color Chart No. 9707) on the upper surface, and R.H.S. Colour Chart No. 65B to 67D on the under surface.
*Eye color.*—Absent.
*Variegation.*—Absent.
*Color presentation.*—Substantially even.
*Overlapping of petals.*—Separate.
*Incision of petal.*—Present, and notched.
*Number of petals.*—One with five lobes per flower.
*Sepal number.*—Five.
*Sepal length.*—Approximately 10 mm on average.
*Sepal apex.*—Acuminate.
*Sepal bases.*—Fused to form a tube.
*Sepal margins.*—Smooth.
*Sepal color.*—R.H.S. Colour Chart No. 144A on both surfaces.
*Pistil number.*—One.
*Pistil length.*—Commonly approximately 1.5 cm on average.
*Style color.*—R.H.S. Colour Chart No. 144C.
*Stigma shape.*—Two lobes.
*Stamen number.*—Four.
*Anther color.*—Yellowish green.
*Peduncle diameter.*—Thin, and commonly approximately 1.7 mm on average.
*Peduncle length.*—Long, and commonly approximately 2.6 mm on average.
*Peduncle color.*—R.H.S. Colour Chart No. 144A.
*Pollen.*—Present in a sparse quantity, and R.H.S. Colour Chart No. 4B in coloration.

*Number of flowers.*—Many with each spike commonly possessing approximately 17 flowers on average.

*Flower fragrance.*—Absent.

*Flowering time.*—Medium.

*Flowering duration.*—Long, with an individual bloom commonly lasting approximately six to eight days.

*Fertility.*—The plant appears to be sterile during observations to date.

Physiological and ecological characteristics:

*Tolerance to cold.*—High, with the plant having withstood a temperature of −5° C.

*Tolerance to heat.*—Medium.

*Resistance to diseases.*—High with respect to Powdery Mildew.

*Resistance to pests.*—High with respect to aphids.

This new variety of Verbena plant is most suitable for flower bedding and potting, particularly in planters, and is further excellent for use as a ground cover.

What is claimed is:

1. A new and distinct variety of Verbena plant, substantially as herein illustrated and described, characterized particularly as to novelty by (A) having an erect growth habit, (B) a plentiful quantity of flowers in a spike with a great profusion of blooms, (C) a long flowering duration, (D) a petal color of vivid purplish red without an eye, and (E) a high resistance to rain, heat, drought, diseases, and pests.

* * * * *